United States Patent

Mylari

[11] 3,966,951
[45] June 29, 1976

[54] ESTERS OF QUINOXALINE-1,4-DIOXIDES

[75] Inventor: Banavara L. Mylari, Waterford, Conn.

[73] Assignee: Pfizer Inc., New York, N.Y.

[22] Filed: Apr. 2, 1975

[21] Appl. No.: 564,363

[52] U.S. Cl............................ 424/250; 260/250 Q; 260/250 QN
[51] Int. Cl.² ............... A61K 31/495; C07D 241/36
[58] Field of Search ............... 260/250 Q, 250 QN; 424/250

[56] References Cited
OTHER PUBLICATIONS
Fisher et al. – Chem. Abst., vol. 80 (1974), p. 409 (article 95884e).

Primary Examiner—Sam Rosen
Attorney, Agent, or Firm—Connolly and Hutz

[57] ABSTRACT

Disclosed herein are novel esters of quinoxaline-1,4-dioxide of the structure

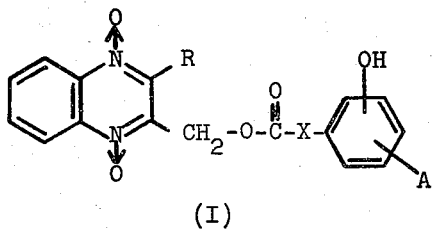

(I)

in which
X is selected from the group consisting of a single bond, lower n-alkylene and $-(CH_2)_p-CH=CH-(CH_2)_q-$ where $p$ and $q$ may have integral values from zero to four with the proviso that $p+q$ is less than or equal to four;

A is selected from the group consisting of hydrogen, hydroxyl, lower alkyl, lower alkoxy, fluorine, chlorine, bromine, iodine, cyano and trifluoromethyl;

and R is selected from the group consisting of hydrogen, lower alkanoyl and α-hydroxy lower alkyl.

When administered to animals, these compounds function as antibacterial agents, promote growth and improve feed efficiency. They are particularly useful in the prophylaxis and treatment of pasturellosis and salmonellosis and are notable for their extremely low toxicity in the test animal.

17 Claims, No Drawings

ESTERS OF QUINOXALINE-1,4-DIOXIDES

BACKGROUND OF THE INVENTION

This invention relates to a novel series of quinoxaline-1,4-dioxides which are useful as antibacterial agents. They are effective, for instance, as urinary tract antiseptics, systemic antiinfectives, animal growth promotants and agents for the control of chronic respiratory disease in turkeys and the improvement of feed efficiency in animals. In particular, it relates to esters formed between various 3-(α-hydroxymethyl)quinoxaline-1,4-dioxides and various acids having certain hyroxyphenyl groups at the ω-position.

The use of quinoxaline-1,4-dioxides as antibacterial agents is known in the art. For instance, U.S. Pat. No. 3,344,022 discloses a series of compounds of the structure

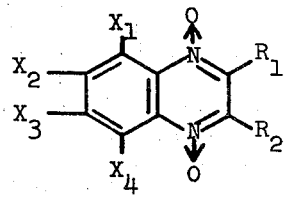

wherein
$R_1$ is selected from the group consisting of hydrogen, alkyl of up to 10 carbon atoms, α-hydroxy lower alkyl, α-lower alkanoyloxy lower alkyl, α-lower alkoxy lower alkyl, and formyl;
$R_2$ is selected from the group consisting of alkyl of up to 10 carbon atoms, lower alkanoyl, α-hydroxy lower alkyl, formyl, α-lower alkanoyloxy lower alkyl, and α-lower alkoxy lower alkyl; and
$X_1$, $X_2$, $X_3$ and $X_4$ are each selected from the group consisting of hydrogen and lower alkyl, which are effective in maintaining weight gain and feed consumption of poultry in the presence of chronic respiratory disease and in controlling chronic respiratory disease, and in accelerating growth and improving feed efficiency of animals. Many of the compounds of the above-mentioned U.S. Patent are used as starting materials in the preparation of the compounds of the present invention.

The use of esters of various 3-hydroxymethyl quinoxaline-1,4-dioxides is known in the art. For instance, U.S. Pat. No. 3,369,400 describes a series of 2-carboxamides of the structure

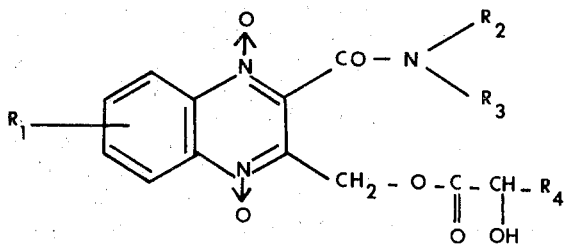

wherein $R_1$ is hydrogen, lower alkyl, lower alkoxy, hydroxy or an acyloxy moiety of a lower aliphatic carboxylic acid;
$R_2$ is hydrogen, an aliphatic moiety or an aliphatic moiety substituted by hydroxy, lower alkoxy, carbalkoxy, monoalkylamino or dialkylamino;
$R_3$ is hydrogen, an aliphatic moiety or an aliphatic moiety substituted by hydroxy, lower alkoxy, carbalkoxy, monoalkylamino or dialkylamino, or $R_2$ and $R_3$ are each lower alkyl linked together with the amide nitrogen to form a 5-, 6- or 7-membered heterocyclic ring or $R_2$ and $R_3$ are each lower alkyl linked together with an amide nitrogen to form a 5-, 6- or 7-membered heterocyclic ring having N or O as a second heteroatom; and
$R_4$ is hydrogen, lower alkyl or substituted or unsubstituted phenyl. U.S. Pat. No. 3,558,624 also describes a series of 2-carboxamides, some of which are structurally isomeric with the above-mentioned compounds, of the structure

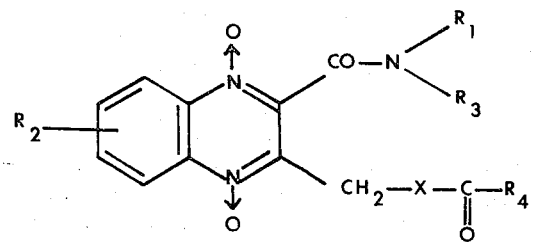

in which
$R_1$ is hydrogen, lower alkyl, lower alkoxy or chlorine;
$R_2$ is hydrogen or a straight or branched chain alkyl radical unsubstituted or substituted by hydroxy, lower alkoxy, acyloxy or mono- or dialkylamino;
$R_3$ is hydrogen or a straight or branched chain alkyl radical unsubstituted or substituted by hydroxy, lower alkoxy, acyloxy or mono- or dialkylamino or, when $R_2$ is hydroxy, $R_3$ is cyclohexyl; or
$R_2$ and $R_3$ together with the amide nitrogen atom form a 5- 6-membered ring,
$R_4$ is alkyl, halogen substituted alkyl, phenyl or hydroxy, methoxy or acetoxy substituted phenyl, and
X is oxygen or sulfur.

Though these carboxamides appear from in vitro tests to be valuable antibacterial agents, it has been found that many of them either are ineffective in test animals against certain target diseases, particularly pasturellosis, salmonellosis and swine dysentery or must be used with extreme caution. In contrast, the compounds of the present invention are safer and show a high in vivo activity against a number of serious veterinary diseases. Therefore, it appears that the prior art on 3-carboxylic acid esters of quinoxaline dioxides is of little value as an indicator of the operative structure-activity relationships in this class of antibacterial agents.

SUMMARY OF THE INVENTION

It has now been found that novel quinoxaline-1,4-dioxide esters of the structure

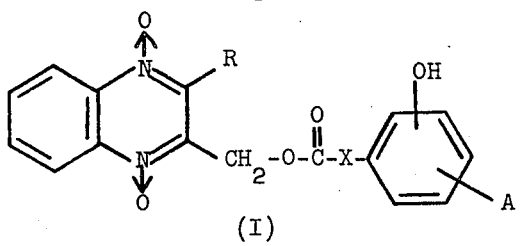

(I)

wherein
- X is selected from the group consisting of a single bond, lower n-alkylene, and —(CH$_2$)$_p$—CH=λ CH—(CH$_2$)$_q$— wherein $p$ and $q$ have integral values from zero to four with the proviso that $p$ plus $q$ is less than or equal to four;
- A is selected from the group consisting of hydrogen, hydroxyl, lower alkyl, lower alkoxy, fluorine, chlorine, bromine, iodine, cyano and trifluoromethyl; and
- R is selected from the group consisting of hydrogen lower alkanoyl and α-hydroxy lower alkyl are useful as antibacterial agents and growth and feed efficiency promoters in animals.

Preferred compounds are those in which A is hydrogen, those in which R is hydrogen, acetyl or hydroxymethyl, those in which the hydroxyl moiety is located at the para position and those in which X is —(CH$_2$)$_2$— or an aliphatic bond. Compounds fulfilling a number or all of these requirements are particularly preferred. The preferred compound is that in which A is hydrogen, the hydroxyl group is located at the para position R is

and X is —(CH$_2$)$_2$—. The terms "lower alkyl," "lower alkanoyl" and "lower alkoxy" as used herein refer to both branched and unbranched radicals of from one to six carbon atoms.

When administered at pharmaceutically effective dosage levels, these compounds are antibacterial agents useful in animal health care. They have been found for instance, to prevent swine dysentery, salmonellosis in poultry, cattle and swine, and also calf pasteurellosis. When administered for therapeutic purposes, oral dose levels of from about 1 to 60 mg/kg and parenteral dose levels of from about 10 to 100 mg/kg of body weight are employed. In addition, they function safely to promote growth and improve feed efficiency. These compounds are usually fed to animals as an additive to a nutritionally-balanced feed at a concentration of from about one to about 150 grams per ton of feed.

DETAILED DESCRIPTION OF THE INVENTION

Compounds of the present invention are prepared by contacting a compound of the structure

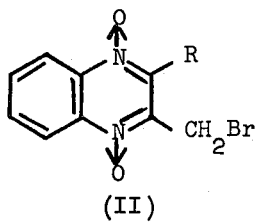

(II)

wherein R is as defined above with a compound of the structure

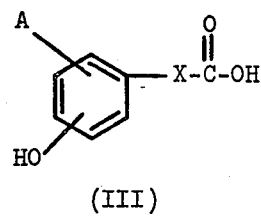

(III)

wherein X and A are as defined above in a reaction-inert solvent in the presence of a base such as potassium carbonate which acts as a hydrogen bromide scavenger at about ambient temperature until the reaction to form the corresponding ester is substantially complete. Reaction-inert solvents are those which are substantially free of adverse effects on reactants and products under the conditions employed. Among the suitable reaction-inert solvents are dimethyl formamide, dimethylsulfoxide and acetonitrile. The product is recovered by adding to the reaction mixture water containing an amount of mineral acid sufficient to substantially neutralize the excess base and precipitate the desired product. The product is collected by suction filtration or other appropriate means, dried and recrystallized from a suitable solvent such as ethanol.

Compounds of formula III are either commercially available or easily prepared from commercially available materials by methods well-known to those skilled in the art. Compounds of formula II are prepared by brominating the methyl analogs of the compounds. The bromination is carried out by contacting the methyl analog with a substantially equimolar amount of bromine in a reaction-inert solvent such as methanol at ambient temperatures until the reaction is substantially complete. The product formed is usually a solid which is collected by filtration, washed with a solvent such as ether and air dried. The methyl analogs of the compounds of formula II are disclosed and their preparation is described in U.S. Pat. No. 3,344,022. Among the compounds disclosed therein, those of particular interest are the ones in which R is hydrogen, hydroxymethyl and acetyl.

The novel compounds of the present invention exhibit excellent activity against swine salmonellosis and swine dysentery which is thought to be caused by *Treponema hyodysenteriae*. Also, they are well-tolerated by rats as indicated by the corticosterone response and adrenal histopathology. Performance of chicks and swine on a regimen containing these compounds is superior to that of non-medicated controls.

The in vitro broad spectrum antibacterial activity of these compounds is demonstrated by determining minimum inhibitory concentrations (MIC) using the Inocula Replicating Device under Anerobic Conditions achieved in the Gas Pac on BHI agar. The MIC is the minimum concentration of the antibacterial in the growth medium at which the test microorganism failed to occur. MIC's against Treponema hyodysenteriae were determined by spreading appropriate dilutions of the microorganism on a growth medium containing about 5% bovine blood and about 3% tryptose agar.

Among the compounds subjected to in vitro screening were the following in which R and X are as defined above and A is hydrogen. The numbers in the column headed by OH indicated the position of the hydroxyl group.

| No. | OH | R | X | m.p.(°C) |
|---|---|---|---|---|
| 1. | 4 | $-\overset{O}{\overset{\|}{C}}CH_3$ | — | 185–186 |
| 2. | 3 | $-\overset{O}{\overset{\|}{C}}CH_3$ | — | 183 |
| 3. | 4 | $-\overset{O}{\overset{\|}{C}}CH_3$ | $-CH_2-$ | 191–192 |
| 4. | 4 | $-CH_2OH$ | — | 186–188 |
| 5. | 4 | $-CH_2OH$ | $-(CH_2)_2-$ | 137–139 |
| 6. | 4 | $-CH_2OH$ | $-CH_2-$ | 187–189 |
| 7. | 4 | $-CH_2OH$ | $-CH=CH-$ | 90–95 |
| 8. | 4 | H | $-(CH_2)_2-$ | 165–166 |
| 9. | 4 | H | $-CH_2-$ | 209–210 |
| 10. | 4 | $-\overset{O}{\overset{\|}{C}}CH_3$ | $-(CH_2)_2-$ | 137–140 |

The following MIC spectra were determined in the in vitro tests.

Primary in vitro Activity (MIC)

| | Staph. aureus 01A005 | Staph. aureus 01A106 | E. Coli 51A-266 | E. Coli 51A-218 | Strep. pyogen 02C203 | Strep. equi 021001 | Strep. zoo 02-H001 | Sal. typhim 58D011 | Sal. dublin 58U001 | Sal. cholsu 58B242 | Aer. hydro 72B001 | Past. mult 59A004 | Past. mult 59A006 |
|---|---|---|---|---|---|---|---|---|---|---|---|---|---|
| 1. | 1.56 | 1.56 | 50 | 50 | 3.12 | <1.56 | <1.56 | 50 | 50 | 50 | 6.25 | 12.5 | 25 |
| 2. | 12.5 | 6.25 | <100 | 50 | 25 | <1.56 | <100 | <100 | <100 | <100 | 3.2 | 12.5 | 25 |
| 3. | 0.78 | 1.56 | 12.5 | 12.5 | 6.25 | <1.56 | <1.56 | 50 | 50 | 50 | <1.56 | 12.5 | 6.25 |
| 4. | 3.2 | 3.2 | 25 | 50 | <1.56 | <1.56 | 100 | 25 | 25 | 50 | 12.5 | 100 | 12.5 |
| 5. | 25 | 25 | 100 | 100 | 50 | 12.5 | 100 | 100 | 100 | 100 | 12.5 | 50 | 50 |
| 6. | 1.56 | 1.56 | 12.5 | 12.5 | <1.56 | <1.56 | 12.5 | 25 | 25 | 25 | 1.56 | 12.5 | 25 |
| 7. | 6.25 | 6.25 | 12.5 | 12.5 | 12.5 | 0.78 | 50 | 12.5 | 25 | 25 | 1.56 | 12.5 | 25 |
| 8. | 12.5 | 12.5 | 100 | 50 | 6.25 | 6.25 | 6.25 | 200 | 100 | 50 | 6.25 | <100 | 50 |
| 9. | 6.25 | 12.5 | 50 | 25 | 3.12 | 6.25 | 6.25 | 25 | 50 | 12.5 | 3.12 | 50 | 12.5 |
| 10. | <0.39 | <0.39 | 25 | 6.25 | <0.39 | <0.39 | <0.39 | 12.5 | 50 | 50 | 1.56 | 25 | 12.5 |

Compound 10 was also found to have an MIC of 0.19 against *Treponema hyodysenteriae*.

Acute systemic infections in mice have been used to evaluate the in vivo therapeutic activity of Compound 10. These infections are produced by the intraperitoneal injection of standard cultures suspended in hog gastric mucin. Treatment was initiated 0.5 hours after inoculation with the infecting organism and two subsequent doses administered at 4 and 24 hours after inoculation. Efficacy was measured in PD$_{50}$ values, the dose of the drug in mg/kg required to protect 50% of the treated mice against otherwise lethal infections. These values were calculated based on the number of mice surviving a 4 day post-treatment holding period. The drugs were administered both orally (po) and subcutaneously (sc). The results of the tests are given below. The range quoted indicates the 95% confidence level for the PD$_{50}$.

| | po | sc |
|---|---|---|
| E. Coli 51A266 | 7.6 ± 4.7 | 13.3 ± 8.6 |
| Sal. cholsu. 58B242 | 8.4 ± 3.2 | 6.9 ± 3.1 |
| Past. multi. 59A006 | 13.0 ± 1.6 | 13.0 ± 1.6 |

Studies have shown that Compound 10 at a level of 250 ppm in chicks is extremely well tolerated. The same results are observed in swine at a level of 150 ppm. In the prophylaxis of two induced diseases, swine dysentery and salmonellosis, excellent results have been obtained. In the dysentery model, 100 percent morbidity and an average of 36 percent mortality was observed in nonmedicated animals. In contrast, no deaths or morbidity was observed in animals on a diet of feed containing 25 ppm or 50 ppm of Compound 10. In the salmonellosis model, 20 percent of the nonmedicated animals died and 50 percent of the survivors were unthrifty. In contrast, none of the animals on a feed containing 50 ppm of Compound 10 died and only 30 percent of them were judged unthrifty. Further, it was observed that 50 ppm of Compound 10 in a feed, increased the feed efficiency of swine by 3 percent; pathological examination of these animals indicated no adverse effects attributable to Compound 10.

The compounds of the present invention may be administered orally or parenterally. When administered orally for prophylactic purposes, the compounds are usually blended into a nutritionally balanced feed at a level of one to 150 grams per ton; when administered orally for therapeutic purposes, appropriately higher dosage levels are employed. The use of one class of quinoxaline dioxides, namely the Schiff bases, is described in detail in the commonly assigned U.S. Pat. Nos. 3,371,090 and 3,344,022, the disclosures of which is incorporated herein by reference. Except for changes necessitated by differences in solubility, the method of use of the compounds of the present invention is much the same.

Typical nutritionally-balanced feeds for hogs are shown in the table below. The prestarter is fed to hogs in the approximate weight range of 10 to 25 pounds and the starter to those in the weight range of about 25 to 50 pounds.

| Ingredients | Pre-Starter 750 lb. Mix (lbs.) | Starter 1,500 lb. Mix (lbs. |
|---|---|---|
| Ground Yellow Corn | 282.9 | 864.75 |
| Cane Sugar | 37.5 | — |
| Soybean Meal (50% C.P.)[1] | 175.5 | 293.25 |
| Dried Skim Milk | 75.0 | 75.0 |

| Ingredients | Pre-Starter 750 lb. Mix (lbs.) | Starter 1,500 lb. Mix (lbs.) |
|---|---|---|
| Dried Whey | 37.5 | 150.0 |
| Dehydrated Alfalfa Meal (17% C.P.)[1] | — | 37.5 |
| Stabilized Animal Fat | 18.75 | 37.5 |
| Limestone | 5.25 | 9.0 |
| Dicalcium Phosphate | 9.4 | 16.5 |
| Iodized Salt | 3.75 | 7.5 |
| Vitamin Premix[2] | 3.75 | 7.5 |
| Delamix[3] | 0.75 | 1.5 |
| | 750.00 | 1500.00 |

[1]C.P. = Crude Protein.
[2]Vitamin Premix:

| | Percent of Premix |
|---|---|
| Vitamin A | 10 |
| Vitamin $D_3$ | 10 |
| Choline Chloride (25%) | 35.25 |
| Niacin | 0.55 |
| Calcium Pantothenate (45%) | 10 |
| Riboflavin | 0.39 |
| Vitamin $B_{12}$ | 0.2 |

[3]Delamix:

| | |
|---|---|
| Manganese | 12 |
| Iodine | 0.24 |
| Iron | 4.0 |
| Copper | 0.4 |
| Zinc | 4.0 |
| Cobalt | 0.04 |

The compounds of the present invention are blended into the above feeds at a concentration of about 1 to 150 gms compound per ton of feed and usually about 20 gms/ton.

A typical feed for use in young poultry, usually chicks, is shown in the table below.

| Ingredient: | Percent of Mix |
|---|---|
| Ground yellow corn | 52.15 |
| Soybean oil meal, 50% | 28.10 |
| Meat scraps, 50% | 4.00 |
| Fish solubles (100-S), 52% | 2.00 |
| Alfafa meal, 17% | 2.00 |
| Stabilized animal fat | 8.00 |
| Multi-fos (dicalcium phosphate) | 2.00 |
| Limestone (38% Ca) | .25 |
| Iodized salt | .50 |
| Vitamin premix | .50 |
| Choline chloride, 25% | .30 |
| Vigofac 6[1] | .15 |
| Delamix | .05 |

[1]Vigofac 6 is the registered trademark of Pfizer Inc., for unidentified poultry and livestock growth factors obtainable from Streptomyces fermentation sources.

The compounds of the present invention are also used in this feed at a concentration of from about 1 to 150 grams and usually about 20 grams per ton of feed. This antibacterial composition is added to the diet at the expense of corn meal.

EXAMPLE I

2- Bromomethyl-Quinoxaline-1,4-Dioxide

To a thick slurry of 106 g. (0.6 mole) of 2-methyl quinoxaline 1,4-dioxide in 400 ml of methanol was added with stirring over a period of 1 hour, 96 g. (0.6 mole) of bromine. The reaction was then stirred for 5 days at room temperature. The reaction mixture was filtered and the collected yellow solid was washed with 200 ml. of ether. This solid was air dried to obtain 50 g. (32percent yield of the title compound, mp-158°–159°.

EXAMPLE II

2-Acetyl-3-Bromomethyl-Quinoxaline-1,4-Dioxide

To a stirred suspension of 2-acetyl-3-methyl-quinoxaline-1,4-dioxide (343 g. 1.57 mole) in 3 l. of methanol was added 89 ml. (1.74 mole) of bromine over a period of two hours. The reaction mixture was then stirred for five days at room temperature. The resulting yellow solid was collected by suction filtration, washed with methanol and ether, and dried to give 331 g. (71 percent yield) of the title compound, mp -164°–166°.

Following the above method, 3-bromomethyl-quinoxaline-1,4-dioxides in which the acetyl group at the two position is replaced by

or

may be prepared.

EXAMPLE III

2-Hydroxymethyl-3-Bromomethyl-Quinoxaline-1,4-Dioxide

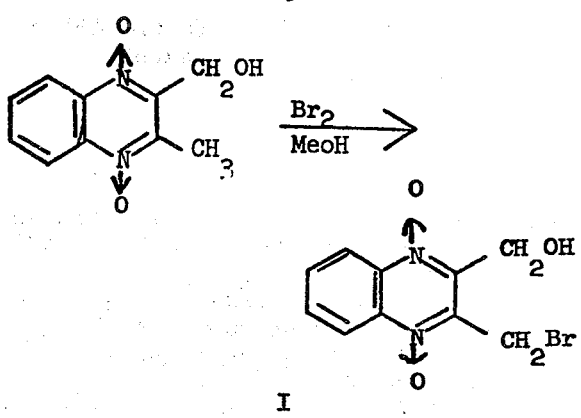

To a stirred suspension of 2-hyroxymethyl-3-methyl-quinoxaline-1,4-dioxide (10.3 g., 0.05 mole) in 100 ml. of methanol was added 1.5 ml. (0.055 mole) of bromine over a period of ten minutes at room temperature. The reaction mixture was then stirred for two days. The resulting yellow solid was collected, washed with methanol and ether, and air dried to give 8.9 g. (62 percent yield of the title compound, mp-138°-140°.

Following the above procedure, 3-bromomethyl-quinoxaline-1,4-dioxides in which the hydyroxymethyl group at the 2-position is replaced by

—CHOHCH$_3$,

—CHOH(CH$_2$)$_2$H,

—CHOH(CH$_2$)$_3$H,

—CHOH(CH$_2$)$_4$H, or

—CHOH(CH$_2$)$_5$H.

EXAMPLE IV

2-Acetyl-3-Hydroxymethyl-Quinoxaline-1,4-Dioxide-p-Hydroxyphenylpropionic Acid Ester To a stirred suspension of potassium carbonate (71.5 g; 0.52M) and p-hydroxyphenylpropionic acid in dimethylformamide (175 ml) was added 2-acetyl-3-bromomethyl quinoxaline 1,4-dioxide (38.6 g; 0.13M) prepared by the method of Example II. The mixture was stirred for one hour at room temperature and the resulting solution was added gradually to water (2500 ml) containing concentrated sulfuric acid (10 ml). The precipitated solid was allowed to granulate for 18 hours and then filtered. The collected solid was recrystallized from ethanol (900 ml) to obtain 49.5 g. of the title compound: yield 63%, mp-137°-140°.

Beginning with the 2-acetyl starting material and following the above procedure, the following compounds were prepared. The number in the column headed by OH indicates the position of the hyroxyl group.

| A | OH | X | mp(°C) |
|---|----|---|--------|
| H | 4 | — | 185–186 |
| H | 3 | — | 183 |
| H | 4 | —CH$_2$— | 191–192 |
| H | 2 | — | 165–167 |

In addition, by following the above procedure and using the compounds of Example II as starting materials, the following series of compounds are prepared by esterifying 2-alkanoyl-3-bromomethyl quinoxaline-1,4-dioxide with the proper carboxylic acid.

| A | OH | X |
|---|----|---|
| H | 2 | —(CH$_2$)$_2$— |
| 3-methyl | 4 | — |
| H | 3 | —(CH$_2$)$_2$— |
| 2-bromo | 4 | —CH$_2$— |
| H | 2 | —(CH=CH)— |
| 3-methyl | H | —(CH$_2$)$_2$— |
| H | 3 | —(CH=CH)— |
| 3-cyano | 4 | — |
| H | 4 | —(CH=CH)— |
| 4-methyl | 3 | —(CH$_2$)$_2$— |
| H | 2 | —CH$_2$— |
| 2-cyano | 4 | — |
| H | 3 | —CH$_2$— |
| 2-iodo | 4 | —(CH$_2$)$_2$— |
| 2-methoxy | 4 | — |
| 4-chloro | 2 | —CH$_2$— |
| 3-trifluoromethyl | 4 | —(CH$_2$)$_4$— |
| 3-methoxy | 4 | — |
| 2-chloro | 4 | —(CH=CH)— |
| 3-chloro | 4 | —(CH$_2$)$_3$— |
| 3-fluoro | 4 | —CH$_2$CH=CHCH$_2$— |
| 4-methoxy | 2 | —(CH$_2$)$_2$— |
| H | 4 | —CH=CH—CH$_2$— |
| 2-methoxy | 4 | —CH$_2$—CH=CH— |
| 4-methoxy | 2 | —(CH$_2$)$_5$— |
| 4-chloro | 3 | — |
| H | 4 | —(CH$_2$)$_6$— |
| 2-trifluoromethyl | | —(CH$_2$)— |
| 2-chloro | 4 | —(CH$_2$)$_2$— |
| 4-ethoxy | 2 | — |
| 2-ethoxy | 4 | —(CH$_2$)$_2$— |
| H | 4 | —(CH$_2$)$_3$— |
| 2-methyl | 4 | —(CH$_2$)$_2$ |
| H | 4 | —(CH$_2$)$_5$— |
| H | 4 | —(CH$_2$)$_4$— |
| 2-iodo | 4 | — |
| 2-cyano | 4 | —(CH$_2$)$_2$— |
| 2-bromo | 4 | —(CH$_2$)$_2$— |
| 4-methyl | 2 | — |
| 4-cyano | 2 | —(CH$_2$)— |
| 3-bromo | 4 | —(CH$_2$)$_2$— |

EXAMPLE V

2-Hyroxymethyl-Quinoxaline-1,4-Dioxide-Carboxylic Acid Esters

Following the method of Example IV, 2-bromomethyl-quinoxaline-1,4-dioxide from Example I was contacted with p-hydroxyphenylacetic acid and p-hydroxyphenylpropionic acid to prepare the following compounds.

| A | OH | X | mp(°C) |
|---|----|---|--------|
| H | 4 | —(CH$_2$)— | 209–210 |
| H | 4 | —(CH$_2$)$_2$— | 165–166 |

In addition, by following the above procedure and contacting 2-bromomethyl-quinoxaline-1,4-dioxide with the carboxylic acids of Example V, a similar series of compounds may be prepared.

EXAMPLE VI 2,3-Bishydroxymethyl-Quinoxaline-1,4-Dioxide-Carboxylic Acid Esters Followng the method of Example IV, 2-hydroxymethyl-3-bromomethyl-quinoxaline-1,4-dioxide was contacted with the appropriate carboxylic acid to prepare the followng compounds.

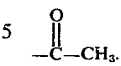

| A | OH | X | mp(°C) |
| --- | --- | --- | --- |
| H | 4 | — | 186–188 |
| H | 4 | —(CH$_2$)$_2$— | 137–139 |
| H | 4 | —(CH=CH— | 90–95 |
| H | 4 | —CH$_2$— | 187–189 |

In addition, by following the above procedure and contacting a 2-α-hydroxy lower alkyl-3-bromomethyl-quinoxaline-1,4-dioxide with the carboxylic acids of Example IV, similar series of compounds are prepared.

What is claimed is:

1. A compound of the structure

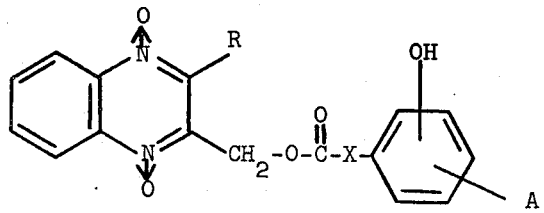

wherein
X is selected from the group consisting of a single bond, n-alkylene having up to six carbon atoms and —(CH$_2$)$_p$—CH=CH—(CH$_2$)$_q$— wherein p and q have integral values from zero to four with the proviso that p plus q is less than or equal to four;
A is selected from the group consisting of hydrogen, hydroxyl, lower alkyl, lower alkoxy, fluorine, chlorine, bromine, iodine, cyano and trifluoromethyl; and
R is selected from the group consisting of hydrogen lower alkanoyl and α-hydroxy lower alkyl.

2. A compound of claim 1 wherein A is hydrogen.

3. A compound of claim 1 wherein the hydroxyl group is in the para position.

4. A compound of claim 1 wherein R is selected from the group consisting of hydrogen, acetyl and hydroxymethyl.

5. A compound of claim 4 wherein R is —CH$_2$OH.

6. A compound of claim 4 wherein R is $$-\overset{\overset{O}{\|}}{C}-CH_3.$$

7. A compound of claim 6 wherein A is hydrogen, the hydroxyl group is in the para position and X is —(CH$_2$)$_2$—.

8. A method of promoting growth and improving feed efficiency of animals comprising administering to said animals a pharmaceutically effective amount of a compound of claim 1.

9. The method of claim 8 wherein said compound is 2-acetyl-3-hydroxymethyl-quinoxaline-1,4-dioxide, 3-(p-hydroxyphenyl)-propionic acid ester.

10. A method of controlling bacterial infections in animals caused by susceptible microorganism comprising administering to said animals a pharmaceutically effective amount of a compound of claim 1.

11. The method of claim 10 wherein said compound is administered at a level of from about 1 to about 100 mg/kg of body weight.

12. The method of claim 11 wherein said compound is administered orally at a level of from about 1 to about 60 mg/kg of body weight.

13. The method of claim 11 wherein said compound is administered parenterally at a level of from about 10 to about 100 mg/kg of body weight.

14. The method of claim 10 wherein said compound is 2-acetyl-3-hydroxymethyl-quinoxaline-1,4-dioxide, 3-(p-hydroxyphenyl) propionic acid ester.

15. A composition containing an effective amount of a compound of claim 1 in a nutritionally balanced animal feed.

16. The composition of claim 15 containing from about 5 to about 150 grams of a compound of claim 1 per ton of feed.

17. The composition of claim 15 wherein said compound is 2-acetyl-3-hydroxymethyl-quinoxaline-1,4-dioxide, 3-(p-hydroxyphenyl)-propionic acid ester.

* * * * *